US009554801B2

(12) United States Patent
Shields et al.

(10) Patent No.: US 9,554,801 B2
(45) Date of Patent: Jan. 31, 2017

(54) EXTRAVASCULAR IMPLANT FOR FACILITATING SUTURED SIDE-TO-SIDE ARTERIOVENOUS FISTULA CREATION AND MAINTAINING PATENCY

(71) Applicant: Cook Medical Technologies LLC, Bloomington, IN (US)

(72) Inventors: Adam Shields, Lafayette, IN (US); Keith Milner, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 134 days.

(21) Appl. No.: 14/659,380

(22) Filed: Mar. 16, 2015

(65) Prior Publication Data

US 2015/0257906 A1    Sep. 17, 2015

Related U.S. Application Data

(60) Provisional application No. 61/952,992, filed on Mar. 14, 2014.

(51) Int. Cl.
*A61B 17/11* (2006.01)

(52) U.S. Cl.
CPC ........ *A61B 17/11* (2013.01); *A61B 2017/1107* (2013.01); *A61B 2017/1139* (2013.01)

(58) Field of Classification Search
CPC ............ A61B 17/11; A61B 2017/1107; A61B 2017/1139; A61B 2017/22077; A61B 2017/1103
See application file for complete search history.

(56) References Cited

U.S. PATENT DOCUMENTS

| | | |
|---|---|---|
| 5,830,222 A | 11/1998 | Makower |
| 6,165,185 A | 12/2000 | Shennib et al. |
| 6,231,587 B1 | 5/2001 | Makower |
| 6,251,116 B1 | 6/2001 | Shennib et al. |
| 6,451,048 B1 | 9/2002 | Berg et al. |
| 6,458,140 B2 | 10/2002 | Akin et al. |
| 6,468,303 B1 | 10/2002 | Amplatz et al. |
| 6,579,311 B1 | 6/2003 | Makower |
| 6,616,675 B1 | 9/2003 | Evard et al. |
| 6,629,951 B2 | 10/2003 | Laufer et al. |
| 6,641,608 B1 | 11/2003 | Pulnev |
| 6,746,464 B1 | 6/2004 | Makower |
| 7,351,247 B2 | 4/2008 | Kupiecki et al. |
| 7,361,181 B2 | 4/2008 | Hindrichs et al. |
| 7,575,586 B2 | 8/2009 | Berg et al. |
| 7,591,827 B2 | 9/2009 | Hill et al. |

(Continued)

FOREIGN PATENT DOCUMENTS

| | | |
|---|---|---|
| JP | 2003-275218 | 9/2003 |
| WO | WO 97/13471 | 4/1997 |

*Primary Examiner* — Jocelin Tanner
(74) *Attorney, Agent, or Firm* — Brinks Gilson & Lione (57) ABSTRACT

An extravascular anastomosis device for facilitating side-to-side arteriovenous fistula creation and maintenance of patency thereof is presented. The device comprises two device halves each containing an anastomosis window which is in fluid connection with an interior space of the device. Further, the device comprises a pair of vessel capture spaces in which portions of the vessels to be joined are captured. The invention also has an embodiment wherein a method of joining a vein and an artery in order to create a fistula is presented.

19 Claims, 3 Drawing Sheets

(56) References Cited

U.S. PATENT DOCUMENTS

| | | |
|---|---|---|
| 7,651,510 B2 | 1/2010 | Bolduc et al. |
| 7,892,246 B2 | 2/2011 | Akin et al. |
| 7,892,247 B2 | 2/2011 | Conston et al. |
| 7,959,053 B2 | 6/2011 | Yasuda |
| 8,016,782 B2 | 9/2011 | Brenneman et al. |
| 8,052,025 B2 | 11/2011 | Yasuda |
| 8,056,790 B2 | 11/2011 | Yasuda |
| 8,074,860 B2 | 12/2011 | Yasuda |
| 8,088,171 B2 | 1/2012 | Brenneman |
| 2002/0143347 A1 | 10/2002 | Cole et al. |
| 2003/0032967 A1 | 2/2003 | Park et al. |
| 2003/0212418 A1 | 11/2003 | Yencho et al. |
| 2003/0229363 A1 | 12/2003 | Sharkawy et al. |
| 2005/0049675 A1 | 3/2005 | Wallace |
| 2005/0101976 A1 | 5/2005 | Kato |
| 2005/0149073 A1 | 7/2005 | Arani et al. |
| 2006/0069401 A1* | 3/2006 | Wright .............. A61B 17/072 606/153 |
| 2008/0171944 A1 | 7/2008 | Brenneman et al. |
| 2010/0106171 A1 | 4/2010 | Arepally et al. |
| 2010/0179569 A1 | 7/2010 | Salky |
| 2010/0181363 A1 | 7/2010 | Yasuda |
| 2010/0268316 A1 | 10/2010 | Brenneman et al. |
| 2012/0065652 A1 | 3/2012 | Cully et al. |
| 2013/0012969 A1 | 1/2013 | Shin |

\* cited by examiner

EXTRAVASCULAR IMPLANT FOR FACILITATING SUTURED SIDE-TO-SIDE ARTERIOVENOUS FISTULA CREATION AND MAINTAINING PATENCY

CROSS REFERENCE TO RELATED APPLICATIONS

This application claims the benefit of U.S. Provisional Patent Application No. 61/952,992, filed on Mar. 14, 2014, the entire contents of which is hereby incorporated by reference.

BACKGROUND OF THE INVENTION

Field of Invention

The present invention relates to medical devices. More particularly, the invention relates to an implant which in one embodiment facilitates sutured side-to-side arteriovenous fistula (AVF) creation and maintains the patency thereof.

Background

End-stage renal disease (ESRD) is a growing problem in the United States and abroad, with the number of patients requiring treatment far outstripping the number of donor kidneys available. Those patients who are unable to receive a kidney transplant are treated by dialysis, with roughly ten times as many patients receiving hemodialysis as all other forms combined.

To minimize treatment time, hemodialysis requires a large blood volume flow rate. Increasing flow is typically achieved through the surgical creation of an arteriovenous shunt. This creates a low resistance pathway, significantly increasing flow through a graft or an arteriovenous fistula.

In practice, AVF is preferred to graft usage because fistulas have better long-term patency rates and reduced incidences of secondary interventions after creation. However, the surgical creation of an AVF and the subsequent venous tissue remodeling required to realize optimized flow rates is only successful in approximately half of surgical procedures. Failures involving AVF are largely due to stenosis via neointimal hyperplasia and thrombosis. A potential cause of neointimal hyperplasia is the exposure of venous tissue to the abnormal hemodynamic conditions resulting from significantly increased flow rates and pulsatility of the added arterial blood flow. In other cases, large flow rates can cause extreme dilation and result in oversized fistulas which fail to achieve the purpose for which they were created.

There exists a need for an improved method of creating arteriovenous fistula and maintaining the patency thereof, including implantation of devices designed to achieve these purposes.

BRIEF SUMMARY OF THE INVENTION

The present invention provides a device for facilitating side-to-side arteriovenous fistula comprising a first device half having a first proximal end and a first distal end, the first device half having a first inner surface and a first outer surface opposite the first inner surface, the first device half comprising a first anastomosis window formed therethrough, the first anastomosis window defining a first arch and a second arch opposite the first arch, the first device half comprising a first barb ridge extending from the inner surface of the first arch and comprising a plurality of first barbs attached to and extending therefrom, and a second barb ridge extending from the inner surface of the second arch and comprising a plurality of second barbs attached to and extending therefrom; a second device half having a second proximal end and a second distal end, the second device half having a second inner surface and a second outer surface opposite the second inner surface, the second device half comprising a second anastomosis window formed therethrough, the second anastomosis window defining a third arch and a fourth arch opposite the third arch, the second device half comprising a third barb ridge extending from the inner surface of the third arch and comprising a plurality of third barbs attached to and extending therefrom, and a fourth barb ridge extending from the inner surface of the fourth arch and comprising a plurality of fourth barbs attached to and extending therefrom, the third arch being opposite and in alignment with the first arch, the second arch being opposite and in alignment with the fourth arch, the first anastomosis window being in alignment with the second anastomosis window; a proximal wall disposed normal to each of the first device half and the second device half, the proximal wall connecting the first proximal end of the first device half to the second proximal end of the second device half; and a distal wall disposed normal to each of the first distal end of the first device half and the second distal end of the second device half, the distal wall connecting the first distal end of the first device half to the second distal end of the second device half, the distal wall being opposite the proximal wall, the first device half being opposite the second device half and spaced apart therefrom to define an interior space between the first device half and the second device half; each of the barb ridges extending into the interior space, the first barb ridge being opposite and spaced apart from the third barb ridge defining a first vessel capture space between the plurality of first barbs and the plurality of third barbs, the second barb ridge being opposite and spaced apart from the fourth barb ridge defining a second vessel capture space between the plurality of second barbs and the plurality of fourth barbs, the first vessel capture space being opposite and in alignment with the second vessel capture space.

In another embodiment the present invention provides a first device half having a first proximal end and a first distal end, the first device half having a first inner surface and a first outer surface opposite the first inner surface, the first device half comprising a first anastomosis window formed therethrough, the first anastomosis window defining a first arch and a second arch opposite the first arch, the first device half comprising a first barb ridge extending from the inner surface of the first arch and comprising a plurality of first barbs attached to and extending therefrom, and a second barb ridge extending from the inner surface of the second arch and comprising a plurality of second barbs attached to and extending therefrom, a first proximal extension extending between the proximal wall and the first anastomosis window, a first distal extension extending between the distal wall and the first anastomosis window; a second device half having a second proximal end and a second distal end, the second device half having a second inner surface and a second outer surface opposite the second inner surface, the second device half comprising a second anastomosis window formed therethrough, the second anastomosis window defining a third arch and a fourth arch opposite the third arch, the second device half comprising a third barb ridge extending from the inner surface of the third arch and comprising a plurality of third barbs attached to and extending therefrom, and a fourth barb ridge extending from the inner surface of the fourth arch and comprising a plurality of fourth barbs attached to and extending therefrom, the third arch being opposite and in alignment with the first arch, the second arch being opposite and in alignment with the fourth arch, the first anastomosis window being in alignment with the second anastomosis window, a second proximal extension extending between the proximal wall and the second anastomosis window, a second distal extension extending between the distal wall and the second anastomosis window; a proximal wall disposed normal to each of the first device half and the second device half, the proximal wall connecting the first proximal end of the first device half to the second proximal end of the second device half; and a distal wall disposed normal to each of the first distal end of the first device half and the second distal end of the second device half, the distal wall connecting the first distal end of the first device half to the second device half, the distal wall being opposite the proximal wall, the first device half being opposite the second device half and spaced apart therefrom to define an interior space between the first device half and the second device half; each of the barb ridges extending into the interior space, the first barb ridge being opposite and spaced apart from the third barb ridge defining a first vessel capture space between the plurality of first barbs and the plurality of third barbs, the second barb ridge being opposite and spaced apart from the fourth barb ridge defining a second vessel capture space between the plurality of second barbs and the plurality of fourth barbs, the first vessel capture space being opposite and in alignment with the second vessel capture space.

In another embodiment, the present invention provides method of facilitating side-to-side fistula along a longitudinal portion of a vein and an artery, the vein having a vein wall, the artery having an artery wall, the method comprising steps of incising the vein wall substantially longitudinally to provide a first vein lip and a second vein lip, defining a vein aperture, incising the vein wall substantially longitudinally to provide a first artery lip and a second artery lip, defining an artery aperture, and implanting an anastomosis device to form the side-to-side fistula, the anastomosis device comprising a first device half having a first proximal end and a first distal end, the first device half having a first inner surface and a first outer surface opposite the first inner surface, the first device half comprising a first anastomosis window formed therethrough, the first anastomosis window defining a first arch and a second arch opposite the first arch; a second device half having a second proximal end and a second distal end, the second device half having a second inner surface and a second outer surface opposite the second inner surface, the second device half comprising a second anastomosis window formed therethrough, the second anastomosis window defining a third arch and a fourth arch opposite the third arch; the first proximal end of the first device half being connected to the second proximal end of the second device half by a proximal wall disposed normal to each of the first device half and the second device half, first distal end of the first device half being connected to the second distal end of the second device half by a distal wall, the proximal wall and the distal wall being disposed normal to each device half disposed normal to each of the first device half and the second device half, the first device half being opposite the second device half and spaced apart therefrom to define an interior space between the first device half and the second device half; the first arch being opposite and in alignment with the third arch, the second arch being opposite and in alignment with the fourth arch, the first anastomosis window being in alignment with the second anastomosis window; the first device half comprising a first barb ridge extending from the inner surface of the first arch into the interior space and a second barb ridge extending from the interior surface of the second arch into the interior space; the second device half comprising a third barb ridge extending from the inner surface of the third arch into the interior space and a fourth barb ridge extending from the inner surface of the fourth arch into the interior space; the first barb ridge being disposed opposite and spaced apart from the third barb ridge, a plurality of first barbs attached to and extending from the first barb ridge, a plurality of third barbs attached to and extending from the third barb ridge defining a first vessel capture space between the plurality of first barbs and the plurality of third barbs; and the second barb ridge being disposed opposite and spaced apart from the fourth barb ridge, a plurality of second barbs attached to and extending from the second barb ridge, a plurality of fourth barbs attached to and extending from the fourth barb ridge defining a second vessel capture space between the plurality of second barbs and the plurality of fourth barbs, the first vessel capture space being opposite and in alignment with the second vessel capture space to facilitate side-to-side fistula.

Further objects, features, and advantages of the present invention will become apparent from consideration of the following description and the appended claims when taken in connection with the accompanying drawings.

DETAILED DESCRIPTION OF THE INVENTION

The following provides a detailed description of currently preferred embodiments of the present invention. The description is not intended to limit the invention in any manner, but rather serves to enable those skilled in the art to make and use the invention.

In this description, when referring to a device, the term distal is used to refer to an end of a component which in use is furthest from the physician during the medical procedure, including within a patient. The term proximal is used to refer to an end of a component closest to the physician and in practice in or adjacent an external manipulation part of the deployment or treatment apparatus. Similarly, when referring to an implant such as an anastomosis device the term distal is used to refer to an end of the device which in use is furthest from the physician during the medical procedure and the term proximal is used to refer to an end of the device which is closest to the physician during the medical procedure.

The terms "substantially" or "about" used herein with reference to a quantity includes variations in the recited quantity that are equivalent to the quantity recited, such as an amount that is equivalent to the quantity recited for an intended purpose or function. "Substantially" or derivatives thereof will be understood to mean significantly or in large part.

The present disclosure generally provides an implant or device which facilitates the formation of an arteriovenous fistula and maintaining the patency thereof. Surgical fistula creation is presently the preferred method of increasing blood flow for ESRD patients who are receiving hemodialysis. The advantages of fistulas over such treatments as grafts are numerous. For instance, of the treatment methods for ESRD patients that might be used to increase blood flow rates, AVFs are associated with decreased morbidity and mortality, and have the superior primary patency rates, the lowest rates of thrombosis, and require the fewest secondary interventions. AVFs generally provide longer hemodialysis access survival rates. Medical data shows that the total number of interventions during the life of the access is considerably lower for AVFs compared with AV grafts and that AVFs have lower rates of infection than AV grafts. The danger of infection is also decreased upon successful formation of an AVF. Thus, it is not surprising that AVFs also lead to lower hospitalization rates among ESRD patients who undergo some form of treatment to increase blood flow rates in order to facilitate hemodialysis.

However, there is a need to improve the ways that AVFs are created and maintained. Fewer than 15% of dialysis fistulas remain patent and can function without problems during the entire period of a patient's dependence on hemodialysis. The mean problem-free patency period after creation of native fistulas is approximately 3 years, whereas prosthetic polytetrafluoroethylene (PTFE) grafts last 1-2 years before indications of failure or thrombosis are noted. After multiple interventions to treat underlying stenosis and thrombosis, the long-term secondary patency rates for native fistulas are reportedly 7 years for fistulas in the forearm and 3-5 years for fistulas in the upper arm. Prosthetic grafts remain patent for up to 2 years.

For prosthetic grafts, fistula failure and eventual occlusion occur most commonly as a result of the progressive narrowing of the venous anastomosis; for native fistulas, failure occurs most commonly as a result of the narrowing of the outflow vein. The primary underlying pathophysiologic mechanism responsible for causing the failure is intimal hyperplasia at the anastomotic site. Additional causes include surgical and iatrogenic trauma, such as repeated venipunctures. Stenoses along the venous outflow and in intragraft locations (for prosthetic PTFE grafts) are also common.

The embodiments of the device described herein are designed in part to overcome these deficiencies. The anastomosis device provides a luminal region with a defined geometry for blood flow therethrough. It also provides a limited amount of contact between the intimal surfaces of the vessels to be connected by the fistula relative to methods of directly connecting the artery and the vein surgically.

Figures 1A, 1B:
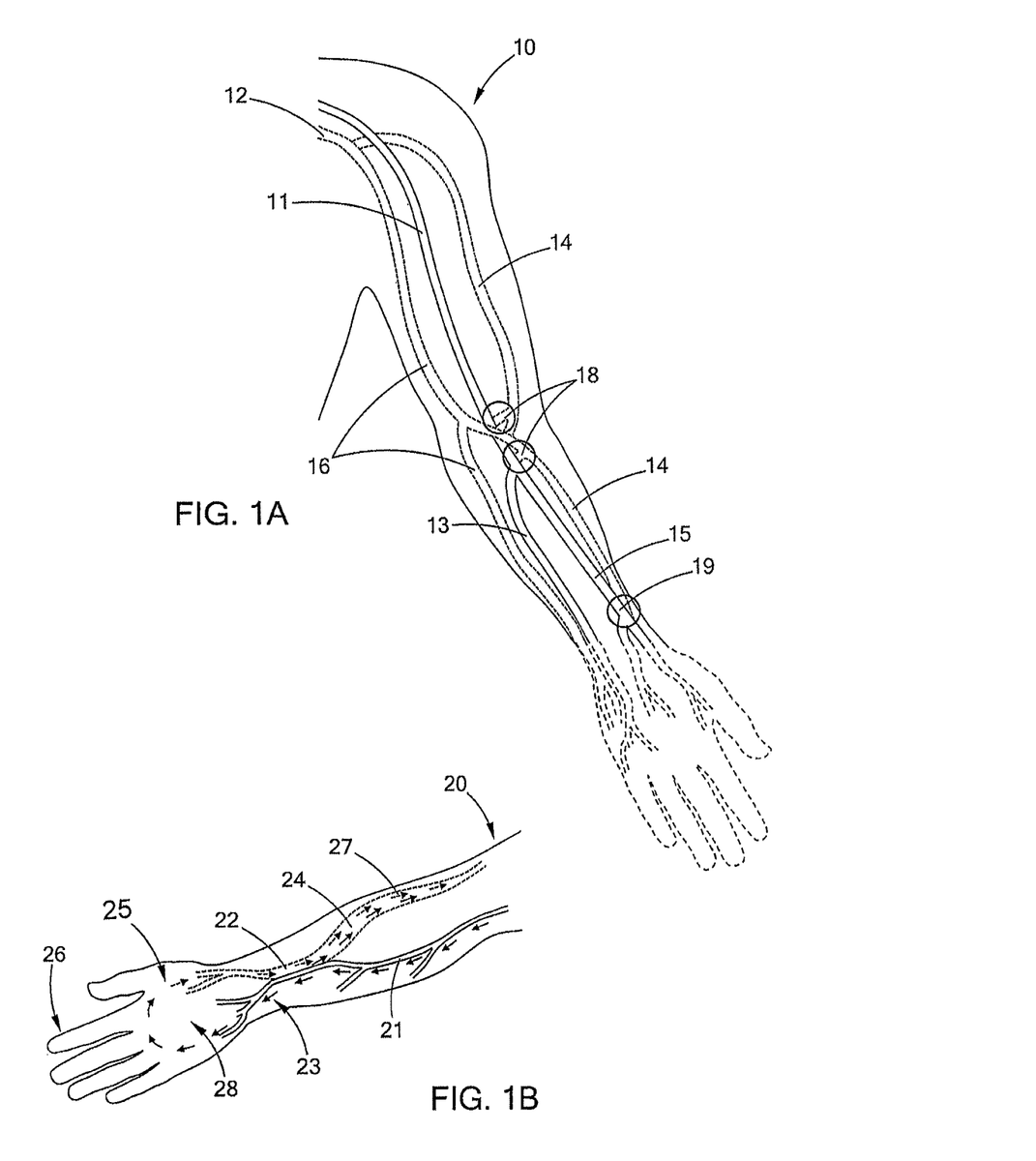
FIG. 1A is diagram of major arteries and veins of the human arm and selected arteriovenous fistulas that may be created therein.
FIG. 1B is a diagram of blood flow through an arteriovenous fistula surgically created in a human forearm.

Referring to FIG. 1A, the veins and arteries of the arm are illustrated. Fistulas in ESRD patients are generally created in the arm. Arm 10 contains a plurality of arteries (illustrated in solid lines) and veins (illustrated in dashed lines.) Brachial artery 11 originates toward the shoulder and splits into an ulnar artery 13 and a radial artery 15 in the region of the elbow. Likewise, axillary vein 12 and cephalic vein 14 run through the shoulder region, and in the area of the elbow, the axillary vein 12 splits into the basilic vein 16. The vessels that were previously split, arteries and veins alike, can undergo anastomosis and form fistulas. Exemplary fistulas illustrated include brachial-cephalic arteriovenous fistula 18, between the brachial artery 11 and the cephalic vein 14, and radial-cephalic fistula 19, between the radial artery and the cephalic vein 14.

FIG. 1B illustrates an example of the blood flow consequences of arteriovenous fistula creation. Artery 21 carries arterial blood 23 away from the heart and through the arm 20 in the direction of hand 26. Arteriovenous fistula 29 connects the artery 21 to vein 22. A portion of the blood flows through fistula 29 and the remainder continues on its natural path through the capillary system 28 in the hand. In the capillaries the blood deoxygenates and flows as venous flow 25 through the vein 22. Due to the fistula, a combined arterial-venous blood flow 27 forms, and as a result of the increased volume and flow rate of blood through the vasculature, an enlarged portion 24 of the vein arises.

Figure 2A:
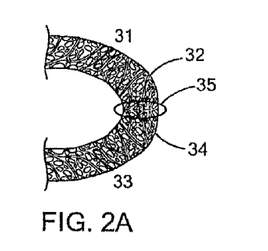
FIGS. 2A-2C are schematic representations of end-to-end, side-to-end, and side-to-side arteriovenous fistulas, respectively.
Figure 2B:
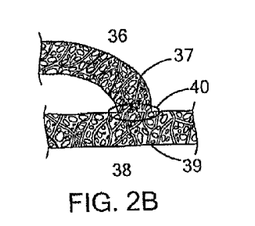
Figure 2C:
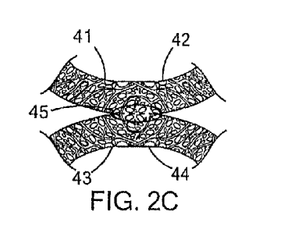

FIGS. 2A-C are examples of different configurations of arteriovenous fistula. FIG. 2A illustrates an artery 31 with an artery end 32 as well as a vein 33 having a vein end 34. The artery end 32 is joined to vein end 34 to form end-to-end arteriovenous fistula 35. Such a fistula configuration can be technically difficult to execute and has an intrinsic disadvantage as artificial creation of an end-to-end fistula naturally requires that the vessels used in its formation be completely severed in order to connect the ends, thereby completely disconnecting the vessels from the rest of the vascular system.

FIG. 2B instead shows artery 38 with artery end 39 and vein 36 with vein wall 37. The artery end 39 is attached to vein 36 through vein wall 37 to form side-to-end arteriovenous fistula 40. This type of fistula is technically simpler to execute for a surgeon but still has the drawback that the vessel whose end it used (in the case illustrated, artery 38 with artery end 39) has its downstream regions disconnected from the rest of the vascular system. This complete rerouting of the blood flow can have negative consequences.

An alternative fistula arrangement, the side-to-side arteriovenous fistula, is illustrated in FIG. 2C. In this example, artery 41 has been perforated through artery wall 42 and joined to vein 43 through vein wall 44 to create side-to-side fistula 45. Because of the side-to-side configuration, a portion of the blood continues to flow in the natural pattern to downstream tissues, unlike the case in which an artery end or a vein end is employed to create the anastomosis. However, even creation of this type of AVF can be difficult using standard surgical techniques. A properly-designed device can simplify the procedure and, importantly, maintain patency of the AVF.

Figure 3:
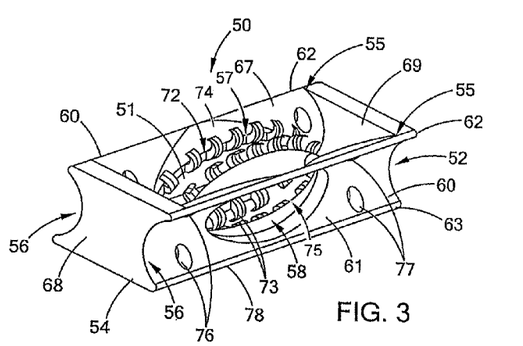
FIG. 3 is a perspective view of one embodiment of a fistula stabilization device.

FIG. 3 illustrates a device 50 in accordance with one embodiment of the present invention. Device 50 has a proximal end 52 and a distal end 54. It should be noted, however, that because of the symmetry between the proximal ends and distal ends, that these designations are arbitrary and employed for purposes of convenience.

The device is made of two device halves 60, including a first device half and a second device half. In the embodiment illustrated in FIG. 3, the device halves 60 extend between proximal end 52 and distal end 54. The first half has an upper arch or first arch 62 and lower arch or second arch 63, which serve to connect the proximal end 52 to the distal end 54. The second device half has an upper arch or third arch 62 and lower arch or fourth arch 63, which serve to connect the proximal end 52 to the distal end 54. The upper arches 62 (the first and third arches) and the lower arches 63 (the second and fourth arches) also frame an empty space in each device half 60 which is first anastomosis window 58 in the first half and second anastomosis window 58 in the second half. The device halves are arranged opposite one another such that the first and second anastomosis windows 58 are aligned, which permits blood to flow through. Between the first and second device halves 60 and in fluid connection with anastomosis windows 58 is a central space of the device which is interior space 51.

The first and second device halves 60 each have an inner surface (first inner surface of the first device half and second inner surface of the second device half) which provides a boundary for the interior space 51 and also have a portion that does not face the interior space 51. This latter portion is referred to as first outer device surface 61 on the first device half and second outer device surface 61 on the second half. On the opposite face to outer device surface is an inner device surface 67. Outer device surface 61 is bounded by portions of upper arch 62 and lower arch 63 and all other portions of device half 60 that are opposite to the interior space 51. The device halves may be divided into The side of the device half which is interior to the device, that is, outer device surface 61 curves away from the interior space 51, giving each device half a "C" shape when viewed head-on and giving the device 50 a modified butterfly shape when viewed in profile. In some embodiments such a butterfly shape may only become apparent when the proximal wall and distal wall of the device have been removed. However, the overall shape of the device and the shape of each device half can take on numerous forms. In the illustrated embodiment, the device halves are substantially concave, but the device halves can also be substantially flat or substantially convex as long as it is possible to maintain extravascular anastomosis and as long as the ability to connect the vessel walls at the portions of the device such as a vessel-connecting space described below is retained. In some embodiments, the device may be substantially as depicted in FIG. 3, but also comprising a projection or ridge extending from the upper arch or the lower arch, or both, off of the outer surface of the device to contact the outer wall of a vessel being used for the creation of the fistula, such that the vessel is more readily guided into the device interior space 51 for securing and fistula creation.

The embodiment of device 50 shown in FIG. 3 further comprises a pair of extensions at each end. Each device half 60 has a proximal extension 55 at proximal end 52 and a distal extension 56 at distal end 54. The proximal extension 55 and the distal extension 56 extend in the proximal and distal directions, respectively, beyond the upper arch 62, the lower arch 63, and the anastomosis window 58. The proximal extension 55 of one device half 60 is bridged to proximal extension 55 of the other device half 60 by proximal device wall 69. The distal extensions 56 are constructed in a similar manner, also being bridged by the distal wall 68. The proximal wall and the distal wall reinforce the overall structure of the anastomosis device and also allow for well-defined spacing apart of the two device halves. The planes of the proximal wall and the distal wall are each substantially normal, or perpendicular, to a plane passing through a portion of the device halves.

Continuing to describe the embodiment illustrated in FIG. 3, the device 50 depicted herein has a projection from the inner surface of the first arch 62 into the interior space 51 which is known as first barb ridge 74. A similar structure is present extending from the interior surface of the second arch and extending into the interior space 51 and is known as second barb ridge 75. A third barb ridge extends from the third arch and a fourth barb ridge extends from the A plurality of first barbs 72 which assist in the gripping and stabilization of portions of vessel walls which have been pulled through the interior space 51 and into the first vessel capture space 57 extend from first barb ridge 74. The points are capable of securing the vascular material but are not sharp enough to pierce and damage it. A device with first barbs 72 could possibly ease and accelerate the suturing process.

The embodiment shown in FIG. 3 has a plurality of second barbs 73 which assist in the gripping and stabilization of portions of vessel walls which have been pulled through the interior space 51 and into the second vessel capture space 59. Analogously to first barbs 72, second barbs 73 are formed along a portion of second arch 63 known as barb ridge 75 and extend with their points within interior space 51. The points are capable of securing the vascular material but are not sharp enough to pierce and damage it. A device may possess only first barbs 72, only second barbs 73, both first barbs 72 and second barbs 73. In one embodiment the device has no barbs. In another embodiment the device has first barbs projecting from a first barb ridge into the interior space, second barbs projecting from a second barb ridge into the interior space, third barbs projecting from a third barb ridge into the interior space, and fourth barbs projecting from a fourth barb ridge into the interior space.

A barb can have two ends, including the end which comprises a portion of the device from which it extends, and the barb can then extend to a second end, which may be a point. Each point is capable of securing the vascular material but a point is not sharp enough to pierce and damage the vessel. The barbs may curve and have a dentate or bladelike shape.

A barb that curves inward is considered to extend in a roughly opposite direction from the outer surface of the device half from which it originates and toward the opposite device half. Such a barb may be integrally formed with the device halves, such as by an additive manufacturing process, including 3D printing, and formed unitarily with the remainder of the device. The device described below and illustrated in FIG. 5 is an example of having inwardly-pointing barbs.

A barb that curves outward is considered to extend from its point of origin on the arch roughly in the direction toward the outer surface of the device half from which it originates and away from the opposite device half. Such a barb may be integrally formed with the device halves, such as by an additive manufacturing process, including 3D printing, and formed unitarily with the remainder of the device. The device shown in FIG. 3 is an example of having outwardly-pointing barbs.

The plurality of first barbs 72 of each device half approach, but do not touch nor overlap with, the plurality of first barbs 72 of the other device half. This creates an interbarb space for a portion of a vessel wall (either an artery or a vein) to be pulled through and prepared for surgical attachment to the corresponding portion of the other vessel which has likewise been pulled through. Hence, it is known as first vessel capture space 57. A similar configuration positions the plurality of second barbs 73 of one device half in close, facing or oppositely-facing, proximity of the plurality of second barbs 73 without touching or overlapping with these opposite barbs. This creates a second vessel capture space 59.

The embodiment of device 50 illustrated in FIG. 3 also possesses a plurality of distal suture ports 76 at the distal end 54 and a plurality of proximal suture ports at proximal end 52. In the embodiment illustrated, the distal suture ports 76 are formed within the distal extensions 56, through outer device surface 61 and connecting to inner extension gap 65. The suture ports 76 and 77 are configured to permit suturing of the device 50 to the vascular tissue to ease handling and provide stability through the implantation process.

As mentioned previously, when there are no features of the device which impart a directionality or introduce an asymmetrical element to it, and the device is outside a surgical context (that is, it is not being used at that moment in a procedure or has not been implanted into a patient), the terms proximal and distal can be switched with one another. The terms first and second can be switched in a similar fashion. However, the outer portion of the device halves, including outer device surfaces 61, will remain an outer or exterior portion, and the inner device surface 67 and interior space 51 will remain interior, regardless of the designation of first/second and proximal/distal.

An anastomosis device 50 with the structural features described herein can be made of a number of different materials. Such a device 50 can be made of a biocompatible and biologically-inert material which will be well-tolerated by the tissues it contacts but will not encourage, for instance, growth of new intimal tissue across its openings. The device 50 can be made of a variety of polymers, including photosensitive polymers which are used for rapid prototyping applications. The polymers can have a stiffness ranging from relatively labile to relatively stiff, as long as the composition maintains the integrity of the anastomosis windows 58. The device 50 may also be coated or impregnated with drugs which will prevent or slow endothelialization of the anastomosis windows 58 and thereby reduce the space available for blood flow through the AVF. The device may be made by a number of processes, including injection molding.

The slits to be cut into the artery walls and vein walls to provide openings for blood flow, when used in a device in accordance with an embodiment of the present invention will be made parallel to the direction of blood flow or substantially longitudinally. Put another way, the slitting is done parallel to a longitudinal axis of the vessel to be slit. In many cases be about one centimeter in length. Therefore, a device 50 will have an anastomosis window 58 which extends for slightly greater than one centimeter in the proximal-to-distal dimension. It is possible that a favorable increase in blood flow through an AVF can be achieved with a fistula which is less than one centimeter wide, in which case it will be acceptable to construct a device 50 with an anastomosis window 58 which is less than 1 centimeter wide as well. Contrarily, certain patients may require that an AVF longer than one centimeter wide be constructed. In such cases, a device which has a longer anastomosis window 58 than one centimeter will be best suited for facilitating hemodialysis in such patients. The overall diameter of the device, as measured from one anastomosis window to another, may be about five to ten millimeters across.

Figure 4A:
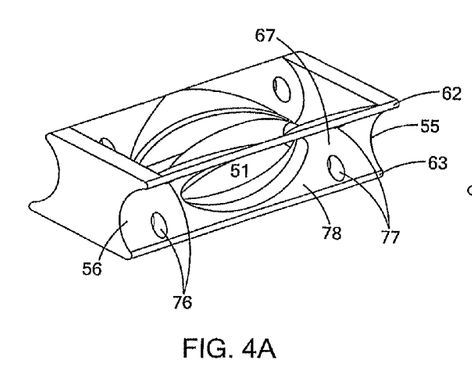
FIGS. 4A-4B are perspective views of two embodiments of device halves having anastomosis windows for use in fistula stabilization devices.
Figure 4B:
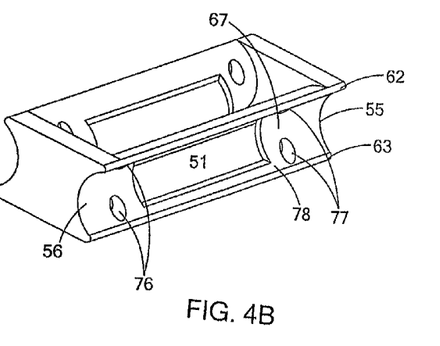

Referring now to FIGS. 4A-4B, perspective views of devices 50 in accordance with embodiments of the present invention are provided. These views illustrate how the outer device surface 61 is formed to define the bounds of the anastomosis window 58. The anastomosis window 58 can take on a variety of shapes. In the preferred embodiment of FIG. 4A, the anastomosis window 58 has a substantially elliptical shape. The dimensions of the ellipse confer certain advantages on the device. For instance, the larger axis of the ellipse provides a way of incorporating the entire length of the AVF which is formed from slitting the vessels within the anastomosis window 58, while the smaller axis of the ellipse further defines the geometry of the anastomosis and ensures that the dimensions of the device do not greatly exceed the height of the vessels involved. Likewise, a device according to the embodiment of FIG. 4B, in which the anastomosis window 58 is a rectangle having a greater length than height dimension, would confer similar advantages to the elliptical window of FIG. 4A. These embodiments, however, are not intended to be limiting. Devices having anastomosis windows 58 in various shapes, including squares, circles, or other polygonal shapes are also envisioned as acceptable alternative embodiments to those illustrated.

Referring now to FIGS. 5A-5E, a method of creating an arteriovenous fistula in accordance with one embodiment of this invention is illustrated. A person having skill in the art will appreciate that variations to the process are possible beyond what is illustrated in FIGS. 5A-5E without deviating from the spirit of the present invention.

The method illustrated in FIGS. 5A-5E employs the device in an extravascular fashion. The vessels are slit and then fed through the anastomosis windows, into the lumen of the device, and back out through the vessel capture space, where the portions of the vessels are secured and joined together. Therefore, no intimal portion of the vessel is in contact with the device, so the device itself functions as a way of remodeling the vessels and keeping the patency of the AVF without being inserted into the lumen of any vessel.

Figure 5A:
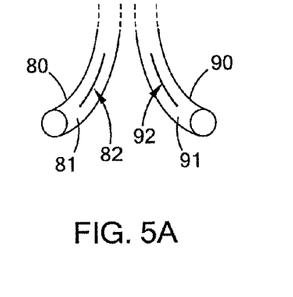
FIGS. 5A-E are cutaway perspective views of the steps of one embodiment of an arteriovenous fistula stabilization device insertion procedure.

FIG. 5A illustrates a vein 80 and an artery 90 which are to be used in the creation of an AVF. The vein 80 is bounded by vein wall 81 and the artery 90 by artery wall 91. A vein slit 82 has been formed through vein wall 81 and an artery slit 92 has been formed through artery wall 91. The slits may be made by any acceptable means, including by scalpel.

Figure 5B:
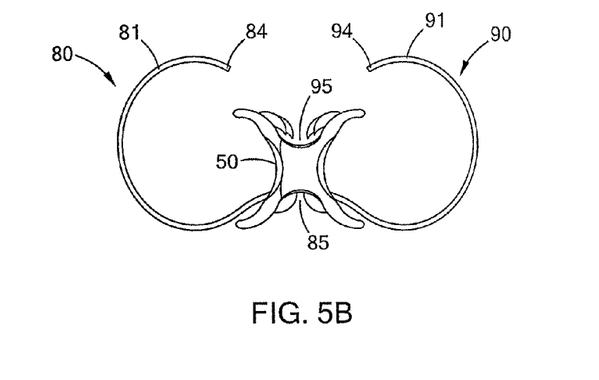

Referring now to FIG. 5B, the vessels have been opened. The vein 80 has been opened along vein slit 82 to divide the vein 80 into second vein lip 83 and first vein lip 84 on either side of the aperture in the vein formed by slitting. Likewise, the artery 90 has been opened along artery slit 92 to create first artery lip 94 and second artery lip 93 on opposite sides of the aperture in the artery formed by its slitting. The second vein lip 83 and the second artery lip 93 have been inserted into the second vessel capture space 59 of device 50 and are gripped and held in place by the plurality of second barbs 73. The position at which the vessels meet is first arteriovenous junction 85.

Figure 5C:
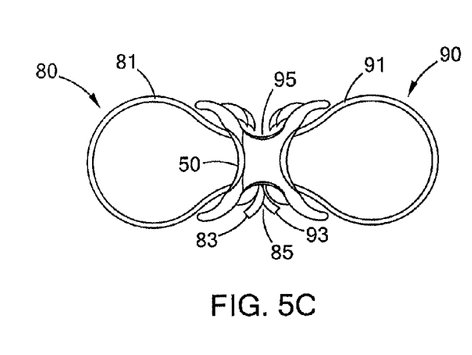
Figure 5D:
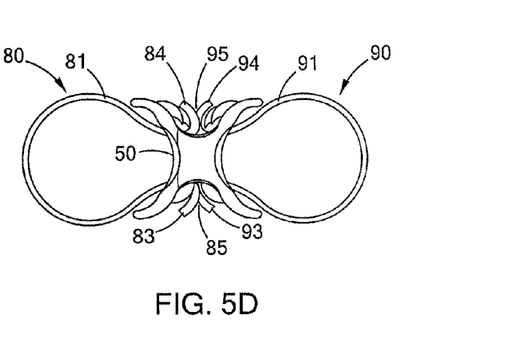

Referring to FIG. 5C, a cutaway view of a device in accordance with the principles of the present disclosure is provided in an illustrative view of one way of implanting said device in a patient in need thereof. In such a view, the proximal device wall and the distal device wall have not been shown in order to provide a view of the implantation procedure. In FIG. 5C, the first vein lip 84 and the first artery lip 94 have been inserted through the anastomosis windows 58 in a similar fashion to their respective second portions in the step of FIG. 5B. FIG. 5D illustrates a further portion of this step wherein the first vein lip 84 and the first artery lip 94 have been fully pulled through and into the first vessel capture space 57. As with the second, the plurality of first barbs 72 secures the first vein lip 84 and the first artery lip 94.

Figure 5E:
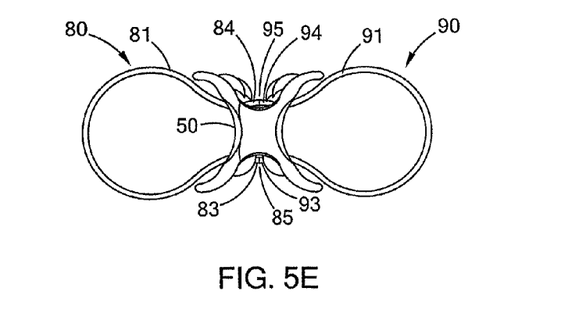

FIG. 5E illustrates the final step in placement of the device 50. The first vein lip 84 and the first artery lip 94 meet at second arteriovenous junction 95. The first arteriovenous junction 85 is secured by a first surgical method and the second arteriovenous junction 95 is secured by a second surgical method. The first surgical method and second surgical method can be such methods as suturing, securing with a surgical glue such as fibrin glue, and any other acceptable method of closing a lesion in tissue. At this point the AVF will have been created and blood will flow through the anastomosis window from the artery 90 into the interior space 51 and then into the vein 80.

As mentioned, further steps may be incorporated into the method in accordance with other embodiments of the present invention. For instance, in the case of a device having at least one suture port, the vein 80 or artery 90 or both can be secured to the device 50 by suturing through the vessel walls and the ports. The vessels will then be thus secured to the device 50 and spaced apart from one another.

As a person skilled in the art will readily appreciate, the above description is meant as an illustration of the implementation of the principles of this invention. This description is not intended to limit the scope or application of this invention in that the invention is susceptible to modification variation and change, without departing from the spirit of this invention, as defined in the following claims.

The invention claimed is:

1. A device for facilitating side-to-side arteriovenous fistula comprising:
a first device half having a first proximal end and a first distal end, the first device half having a first inner surface and a first outer surface opposite the first inner surface, the first device half comprising a first anastomosis window formed therethrough, the first anastomosis window defining a first arch and a second arch opposite the first arch, the first device half comprising a first barb ridge extending from the inner surface of the first arch and comprising a plurality of first barbs attached to and extending therefrom, and a second barb ridge extending from the inner surface of the second arch and comprising a plurality of second barbs attached to and extending therefrom;
a second device half having a second proximal end and a second distal end, the second device half having a second inner surface and a second outer surface opposite the second inner surface, the second device half comprising a second anastomosis window formed therethrough, the second anastomosis window defining a third arch and a fourth arch opposite the third arch, the second device half comprising a third barb ridge extending from the inner surface of the third arch and comprising a plurality of third barbs attached to and extending therefrom, and a fourth barb ridge extending from the inner surface of the fourth arch and comprising a plurality of fourth barbs attached to and extending therefrom, the third arch being opposite and in alignment with the first arch, the second arch being opposite and in alignment with the fourth arch, the first anastomosis window being in alignment with the second anastomosis window;
a proximal wall disposed normal to each of the first device half and the second device half, the proximal wall connecting the first proximal end of the first device half to the second proximal end of the second device half; and
a distal wall disposed normal to each of the first distal end of the first device half and the second distal end of the second device half, the distal wall connecting the first distal end of the first device half to the second device half, the distal wall being opposite the proximal wall, the first device half being opposite the second device half and spaced apart therefrom to define an interior space between the first device half and the second device half;
each of the barb ridges extending into the interior space, the first barb ridge being opposite and spaced apart from the third barb ridge defining a first vessel capture space between the plurality of first barbs and the plurality of third barbs, the second barb ridge being opposite and spaced apart from the fourth barb ridge defining a second vessel capture space between the plurality of second barbs and the plurality of fourth barbs, the first vessel capture space being opposite and in alignment with the second vessel capture space.

2. The device of claim 1 wherein the proximal ends of the device halves define a pair of proximal extensions extending from each anastomosis window to the proximal wall, and wherein the distal ends of the device halves define a pair of distal extensions extending from each anastomosis window to the distal wall.

3. The device of claim 1 further comprising a plurality of suture ports at the proximal and distal ends.

4. The device of claim 2 further comprising a plurality of suture ports through the proximal and distal extensions.

5. The device of claim 1 wherein each of the plurality of first barbs terminates in a point directed toward the inner surface of the opposite device half.

6. The device of claim 1 wherein each of the plurality of first barbs terminates in a point directed toward the interior space of the device.

7. The device of claim 1 having anastomosis windows that are substantially elliptical.

8. The device of claim 1 having anastomosis windows that are substantially rectangular.

9. A device for facilitating side-to-side arteriovenous fistula comprising:
a first device half having a first proximal end and a first distal end, the first device half having a first inner surface and a first outer surface opposite the first inner surface, the first device half comprising a first anastomosis window formed therethrough, the first anastomosis window defining a first arch and a second arch opposite the first arch, the first device half comprising a first barb ridge extending from the inner surface of the first arch and comprising a plurality of first barbs attached to and extending therefrom, and a second barb ridge extending from the inner surface of the second arch and comprising a plurality of second barbs attached to and extending therefrom, a first proximal extension extending between a proximal wall and the first anastomosis window, a first distal extension extending between a distal wall and the first anastomosis window;
a second device half having a second proximal end and a second distal end, the second device half having a second inner surface and a second outer surface opposite the second inner surface, the second device half comprising a second anastomosis window formed therethrough, the second anastomosis window defining a third arch and a fourth arch opposite the third arch, the second device half comprising a third barb ridge extending from the inner surface of the third arch and comprising a plurality of third barbs attached to and extending therefrom, and a fourth barb ridge extending from the inner surface of the fourth arch and comprising a plurality of fourth barbs attached to and extending therefrom, the third arch being opposite and in alignment with the first arch, the second arch being opposite and in alignment with the fourth arch, the first anastomosis window being in alignment with the second anastomosis window, a second proximal extension extending between the proximal wall and the second anastomosis window, a second distal extension extending between the distal wall and the second anastomosis window;

the proximal wall disposed normal to each of the first device half and the second device half, the proximal wall connecting the first proximal end of the first device half to the second proximal end of the second device half; and the distal wall disposed normal to each of the first distal end of the first device half and the second distal end of the second device half, the distal wall connecting the first distal end of the first device half to the second device half, the distal wall being opposite the proximal wall, the first device half being opposite the second device half and spaced apart therefrom to define an interior space between the first device half and the second device half;

each of the barb ridges extending into the interior space, the first barb ridge being opposite and spaced apart from the third barb ridge defining a first vessel capture space between the plurality of first barbs and the plurality of third barbs, the second barb ridge being opposite and spaced apart from the fourth barb ridge defining a second vessel capture space between the plurality of second barbs and the plurality of fourth barbs, the first vessel capture space being opposite and in alignment with the second vessel capture space.

10. A method of facilitating side-to-side fistula along a longitudinal portion of a vein and an artery, the vein having a vein wall, the artery having an artery wall, the method comprising:

incising the vein wall substantially longitudinally to provide a first vein lip and a second vein lip, defining a vein aperture;

incising the vein wall substantially longitudinally to provide a first artery lip and a second artery lip, defining an artery aperture;

implanting an anastomosis device to form the side-to-side fistula, the anastomosis device comprising a first device half having a first proximal end and a first distal end, the first device half having a first inner surface and a first outer surface opposite the first inner surface, the first device half comprising a first anastomosis window formed therethrough, the first anastomosis window defining a first arch and a second arch opposite the first arch, the first device half comprising a first barb ridge extending from the inner surface of the first arch and comprising a plurality of first barbs attached to and extending therefrom, and a second barb ridge extending from the inner surface of the second arch and comprising a plurality of second barbs attached to and extending therefrom; a second device half having a second proximal end and a second distal end, the second device half having a second inner surface and a second outer surface opposite the second inner surface, the second device half comprising a second anastomosis window formed therethrough, the second anastomosis window defining a third arch and a fourth arch opposite the third arch, the second device half comprising a third barb ridge extending from the inner surface of the third arch and comprising a plurality of third barbs attached to and extending therefrom, and a fourth barb ridge extending from the inner surface of the fourth arch and comprising a plurality of fourth barbs attached to and extending therefrom, the third arch being opposite and in alignment with the first arch, the second arch being opposite and in alignment with the fourth arch, the first anastomosis window being in alignment with the second anastomosis window; a proximal wall disposed normal to each of the first device half and the second device half, the proximal wall connecting the first proximal end of the first device half to the second proximal end of the second device half; and a distal wall disposed normal to each of the first distal end of the first device half and the second distal end of the second device half, the distal wall connecting the first distal end of the first device half to the second device half, the distal wall being opposite the proximal wall, the first device half being opposite the second device half and spaced apart therefrom to define an interior space between the first device half and the second device half; each of the barb ridges extending into the interior space, the first barb ridge being opposite and spaced apart from the third barb ridge defining a first vessel capture space between the plurality of first barbs and the plurality of third barbs, the second barb ridge being opposite and spaced apart from the fourth barb ridge defining a second vessel capture space between the plurality of second barbs and the plurality of fourth barbs, the first vessel capture space being opposite and in alignment with the second vessel capture space to facilitate side-to-side fistula.

11. The method of claim 10 wherein implanting comprises:

disposing the second artery lip through the first anastomosis window and the second vein lip through the second anastomosis window such that the second artery lip and the second vein lip are disposed in the second vessel capture space;

joining the second vein lip to the second artery lip;

disposing the first artery lip through the first anastomosis window and the first vein lip through the second anastomosis window such that the first artery lip and the first vein lip are disposed in the first vessel capture space; and joining the first vein lip to the first artery lip.

12. The method of claim 11 further comprising a step of securing the second vein lip on at least one of the plurality of barbs after placing the second vein lip and the second artery lip portion through an anastomosis window and into the second vessel capture space of the anastomosis device.

13. The method of claim 12 further comprising a step of securing the second artery lip on at least one of the plurality of barbs after placing the second artery lip and the second vein lip through an anastomosis window and into the second vessel capture space of the anastomosis device.

14. The method of claim 13 further comprising a step of securing the first vein lip on at least one of the plurality of barbs after placing the first vein lip and the first artery lip through an anastomosis window and into the first vessel capture space of the anastomosis device.

15. The method of claim 14 further comprising a step of securing the first artery lip on at least one of the plurality of barbs after placing the first vein lip and the first artery lip through an anastomosis window and into the first vessel capture space of the anastomosis device.

16. The method of claim 14 further comprising providing a device having suture ports substantially at the proximal end and distal end of the device.

17. The method of claim 16 wherein the artery and the vein are secured to the device by suturing through the suture ports.

18. The method of claim 17 wherein joining the vein lips to the artery lips comprises suturing.

19. The method of claim 17 wherein joining the vein lips to the artery lips comprises connecting with surgical glue.

* * * * *